(12) United States Patent
Epstein et al.

(10) Patent No.: US 6,835,193 B2
(45) Date of Patent: *Dec. 28, 2004

(54) METHODS FOR CONTROLLED DEPTH INJECTIONS INTO INTERIOR BODY CAVITIES

(75) Inventors: Stephen Epstein, Rockville, MD (US); Shmuel Fuchs, Rockville, MD (US); Ran Kornowski, Ramat-Hasharon (IL)

(73) Assignee: Myocardial Therapeutics, Inc., La Jolla, CA (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/000,851

(22) Filed: Oct. 23, 2001

(65) Prior Publication Data

US 2003/0028172 A1 Feb. 6, 2003

Related U.S. Application Data

(60) Provisional application No. 60/304,641, filed on Jul. 10, 2001, and provisional application No. 60/304,607, filed on Jul. 10, 2001.

(51) Int. Cl.[7] .......................... A61M 31/00; A61M 5/00; A61M 5/178
(52) U.S. Cl. .................... 604/507; 604/117; 604/164.01
(58) Field of Search ............................ 604/22, 48, 200, 604/95.01, 73, 181, 187, 131, 141, 143, 148, 264, 507, 523, 533, 158, 164.01, 280; 606/167, 170; 600/434, 858

(56) References Cited

U.S. PATENT DOCUMENTS

| | | |
|---|---|---|
| 4,314,565 A | 2/1982 | Lee |
| 4,481,946 A | 11/1984 | Altshuler et al. |
| 4,486,188 A | 12/1984 | Altshuler et al. |
| 4,513,754 A | 4/1985 | Lee |
| 4,630,616 A | 12/1986 | Tretinyak |
| 4,664,128 A | 5/1987 | Lee |
| 4,900,303 A | 2/1990 | Lemelson |
| 5,257,632 A | 11/1993 | Turkel et al. |
| 5,331,972 A | 7/1994 | Wadhwani et al. |
| 5,419,777 A | 5/1995 | Hofling |
| 5,531,672 A | 7/1996 | Lynn |
| 5,591,159 A | 1/1997 | Taheri |
| 5,607,421 A | 3/1997 | Jeevanandam et al. |

(List continued on next page.)

FOREIGN PATENT DOCUMENTS

| | | |
|---|---|---|
| WO | WO 01/24851 A1 | 4/2001 |
| WO | WO 01/26706 A2 | 4/2001 |

*Primary Examiner*—Brian L. Casler
*Assistant Examiner*—Catherine S. Williams
(74) *Attorney, Agent, or Firm*—Gray Cary Ware & Freidenrich, LLP

(57) ABSTRACT

A flexible tissue injection catheter is used to accomplish injections at a precisely controlled depth of precisely controlled volumes of a therapeutic or diagnostic agent into an interior body cavity, such as the epicardium or myocardium of the heart. In one embodiment, the invention method includes repeated injections at spaced intervals along the myocardium or epicardium of sterile fluid containing autologous bone marrow aspirate to promote angiogenesis. For myocardial injection, depth penetration is controlled by using a catheter that allows the operator to control depth penetration by means of an adjustable needle stop attached to the catheter handle. In another embodiment depth penetration during epicardial injections is controlled by use of an injection catheter having an operator-controlled adjustable needle stop that produces a sensible signal, such as a visible or audible signal, marking each increment of needle tip exposed by operation of the adjustable needle stop.

38 Claims, 5 Drawing Sheets

U.S. PATENT DOCUMENTS

| | | |
|---|---|---|
| 5,693,029 A | 12/1997 | Leonhardt |
| 5,782,824 A | 7/1998 | Abela et al. |
| 5,810,836 A | 9/1998 | Hussein et al. |
| 5,840,059 A | 11/1998 | March et al. |
| 5,876,373 A | 3/1999 | Giba et al. |
| 5,885,272 A | 3/1999 | Aita et al. |
| 5,904,670 A | 5/1999 | Schreiner |
| 5,968,059 A | 10/1999 | Ellis et al. |
| 5,980,548 A | 11/1999 | Evans et al. |
| 6,086,582 A | 7/2000 | Altman et al. |
| 6,102,887 A * | 8/2000 | Altman ........................ 604/22 |
| 6,117,130 A | 9/2000 | Kung |
| 6,126,654 A | 10/2000 | Giba et al. |
| 6,171,251 B1 | 1/2001 | Mueller et al. |
| 6,203,556 B1 | 3/2001 | Evans et al. |
| 6,217,554 B1 | 4/2001 | Green |
| 6,224,584 B1 | 5/2001 | March et al. |
| 6,226,554 B1 | 5/2001 | Tu et al. |
| 6,302,870 B1 | 10/2001 | Jacobsen et al. |
| 6,526,320 B2 | 2/2003 | Mitchell |

\* cited by examiner

METHODS FOR CONTROLLED DEPTH INJECTIONS INTO INTERIOR BODY CAVITIES This application claims priority under 35 U.S.C. §119(e) of U.S. Provisional Application Ser. No. 60/304,641, filed Jul. 10, 2001, and U.S. Provisional Application Ser. No. 60/304,607, filed Jul. 10, 2001, the entire contents of which are incorporated herein by reference.

This application is related to U.S. application Ser. No. 10/004,525 entitled "STERILE ASPIRATION/ REINJECTION SYSTEM", U.S. application Ser. No. 10/000,786 entitled FLEXIBLE TISSUE INJECTION CATHETER WITH CONTROLLED DEPTH PENETRATION, and U.S. application Ser. No. 09/999,765 entitled METHODS FOR STERILE ASPIRATION/ REINJECTION OF BODILY FLUID, filed on even date herewith, the entire contents of each of which is incorporated herein by reference.

FIELD OF THE INVENTION

The invention relates generally to medical system and procedures and more particularly to devices and methods of their use for injection of a therapeutic agent into the surface of an interior body cavity of a living being.

BACKGROUND INFORMATION

Market expansion in cardiovascular and cardiothoracic surgery in past years has largely been driven by increases in open-heart surgical bypass procedures, but new opportunities for growth will come from products associated with least-invasive procedures. The positive outcomes seen thus far with these techniques, accompanied by continued physician acceptance, will lead to a gradual erosion of the market for traditional open-heart surgery.

Driven by capitation and cost-cutting measures associated with managed care, these evolving techniques and procedures not only hold the promise of reduced trauma to patients, but also reduce the significant costs associated with traditional open-heart surgery. Markets for least-invasive approaches to cardiothoracic surgery, including equipment and disposables, are predicted to grow at tremendous rates through the end of this century.

Within the past few years, an increasing number of centers worldwide have begun performing revolutionary techniques, such as beating-heart coronary artery bypass and laser transmyocardial revascularization (TMR). These developing procedures offer the potential of expanding the size of the eligible patient base by providing a viable alternative to patients unable to undergo open heart surgery, accelerated by significantly reduced patient trauma and, of course, the promise of lower costs.

Bone marrow cells and liquid aspirate are believed to be the source of angiogenic peptides known as growth factors. In addition, recent studies have shown that bone marrow cells include stem cells that differentiate into angioblasts. Angiogenesis represents the postnatal formation of new blood vessels by sprouting from existing capillaries or venules. During angiogenesis, endothelial cells are activated from a quiescent microvasculature (turnover of thousands of days) to undergo rapid proliferation (turnover of a few days).

In one technique currently in clinical stage testing employs transplantation of autologous bone marrow cells into the heart to restore heart function. Autologous bone marrow cells obtained by aspiration from the patient's hip bone are transplanted into transventricular scar tissue for differentiation into cardiomyocytes to restore myocardial function (S. Tomita, et al., *Circulation* 100:19 Suppl II247–56, 1999. In another technique, autologous bone marrow cells are harvested and transplanted into an ischemic limb or cardiac tissue as a source of angiogenic growth factors, such as VEGF (A. Sasame, et al., *Jpn Heart J, Mar* 40:2 165–78, 1999).

Various types of bone marrow biopsy, aspiration and transplant needles and needle assemblies have been proposed and are currently being used. Many of them include a cannula, stylet with cutting tip, or trocar, that can be used to cut a bone marrow core sample. For withdrawal of liquid sample of bone marrow, an aspiration device comprising a hollow needle attached to a device for creating a negative pressure to aspirate the liquid bone marrow.

However, current procedures used for harvesting, purification and reinjection of autologous bone marrow cells require sedation of the patient for a period of three to four hours while the bone marrow aspirate is prepared for reinjection. In addition, the present procedure involves great risk of infection for the subject because the harvested bone marrow material is routinely aspirated in an operating or recovery room and then transferred after aspiration to a laboratory where the aspirate is placed into a centrifuge for gravity separation of bone marrow cells from the aspirate. In many cases the bone marrow aspirate is transferred into a specially designed centrifuge tube for the gravity separation. The separated bone marrow cells are then removed from the centrifuge tube into a syringe and delivered back to the recovery room or operating room for delivery to the patient. Generally, the processed cells are delivered to the body location where reperfusion is required by catheter. For example, delivery of bone marrow cells by pericardial catheter into the subject's myocardium can be used to stimulate angiogenesis as a means of bypassing a blocked artery by collateral capillary development. However, prior art methods utilizing transfer of the material from the site of the aspiration for treatment at another site and/or into another vessel for separation risk introduction of pathogens with consequent increased risk of infection for the patient.

Angiogenic peptides like VEGF (vascular endothelial growth factor) and bFGF (basic fibroblast growth factor) have also entered clinical trials for treatment of coronary artery disease. Attempts are being made to devise clinically relevant means of delivery and to effect site-specific delivery of these peptides to ischemic tissue, such as heart muscle, in order to limit systemic side effects. Typically cDNA encoding the therapeutic peptide is either directly injected into the myocardium or introduced for delivery into a replication-deficient adenovirus carrying the cDNA to effect myocardial collateral development in a subject suffering progressive coronary occlusion. It is also known to transfect autologous bone marrow cells obtained as described above with such adenovirus for in vivo expression of the angiogenic peptide at the site of blockage. However, the handling of adenovirus vectors is generally considered a risk to the medical team members responsible for handling the vectors and/ or transfecting the bone marrow cells with the vectors. For this reason, current practice is to do such work "under the hood" to curtail possible escape of the adenovirus, thus requiring transport of the bone marrow to a laboratory setting for transfection and then return to the patient setting for reinjection of the transfected cells.

Moreover, the amount of extraneously introduced angiogenic growth factor, such as VEGF, that can be tolerated by the subject is very small. At high doses VEGF is known to cause a drop in blood pressure. Over dosage has proven to be fatal in at least one clinical trial. Thus strict control of the amount of growth factor delivered is of great importance. In addition, since the delivery site is located along the surface of an interior body cavity, such as the pericardium, a deflectable intravascular catheter with an infusion needle is customarily used, but it is difficult to tell whether the needle penetrates substantially orthogonally to the tissue surface so that the therapeutic is delivered at a single location or at an angle so that the therapeutic is delivered across a greater area. Thus, it is difficult to control the amount of therapeutic introduced at a single location.

In addition, controlling the depth of needle penetration is complicated by the tendency of prior art deflectable infusion catheters to withdraw the needle into the catheter when the catheter is deflected to approach the wall of an internal organ, thereby increasing the effective length of the catheter. In compensation for needle withdrawal, it is current practice to advance the needle from the tip of the catheter an extra distance to allow for withdrawal of the needle back into the catheter as the catheter is deflected. As a result, it is difficult to control the exact depth of needle penetration. In some cases, where the catheter is advanced into the pericardial space to deliver a therapeutic fluid into the myocardium, the needle has actually punctured the wall of the heart due to over-penetration, with the result that the therapeutic fluid is not introduced into the myocardium at all.

Many other therapeutic substances are also introduced into the surface of interior body cavities. For example, the reverse of angiogenesis is practiced for a number of therapeutic purposes, such as the prevention of restenosis following a reperfusion procedure or in treatment of diabetic retinopathy and cancer. In anti-restenosis, the growth of new blood vessels is blocked or curbed and the formation of new tissue (e.g., a growing tumor, neointima on the surface of a stent or vascular prosthesis, etc.) is limited or eliminated by introduction of "reverse angiogenesis" agents, such as angiostatin, endostatin or, antarin, a locally administered mitotoxin that inhibits cell proliferation into the tissue.

Various types of tissue injection catheters have been developed to address the problem of injecting angiogenic agents into the interior of a body cavity, such as blood vessels or the myocardium of the heart. For example, U.S. Pat. No. 6,217,554 discloses a catheter designed to deliver therapeutic substances extravascularly. Once advanced through the vasculature, an advancement mechanism on the catheter is actuated to advance a plurality of hollow needles positioned on a slideably mounted tubular member, wherein the needles are biased to curve outwardly to penetrate the vasculature and deliver the therapeutic substance extravascularly. Another type of drug injection catheter disclosed in PCT application US99/22679 (WO 01/24852) discloses a needle slideably mounted on tubing contained within the catheter and utilizes a tracking system of transducers in the distal end of the catheter as well as transducers external to the patient to target angiogenic drugs to ischemic tissue. Yet another type of drug delivery catheter disclosed in PCT application US00/28301 and U.S. Pat. No. 5,782,824 includes a distal helical coil that can be operated from the proximal end of the catheter to engage and penetrate the myocardium.

Despite these advancements in the art, there is a need in the art for new and better equipment for use in handling and treating autologous bone marrow and for controlled delivery of fluid containing cells, nucleic acid encoding therapeutic peptides, and the like, into interior body cavities, especially into the vasculature and the interior or exterior of the heart to induce or curtail angiogenesis. In particular, there is a need in the art for an injection catheter with an injection needle that penetrates a controlled distance into tissue, for example, into the wall of a body cavity. In addition, there is need for new and better catheters adapted to inject a controlled amount of a therapeutic substance to a defined area of an interior body cavity or to aspirate fluids from an interior body cavity. The present invention satisfies these needs and provides additional advantages.

SUMMARY OF THE INVENTION

The invention overcomes many of the problems in the art by providing methods for injecting a therapeutic fluid a controlled distance into the surface of an interior body cavity in a subject in need thereof. In one embodiment, the invention methods for controlled depth injection comprise (a) introducing a catheter into the interior of a body cavity by advancing the catheter through the vascular system of the subject, said catheter comprising:

i) an elongate hollow catheter body having a proximal end and a distal end with a flexible portion at the distal tip thereof, said catheter body being sized and constructed to be advanced intravascularly into an interior body cavity of a subject;

ii) a hollow needle housed throughout the catheter body, said needle having a distal portion with a sharp tip and a proximal portion in fluid communication with a fluid source, said needle further having a retracted needle position wherein the sharp tip of the needle is disposed within the catheter body, and an advanced needle position wherein the sharp tip of the needle extends a fixed distance beyond a distal end face of the catheter body, iii) a needle stop attached to the needle that tethers the distal portion of needle during flexure while the proximal portion of the needle remains freely slideable within the catheter body, and iv) an advancement mechanism attached to the needle for advancing the needle distally a fixed distance to the advanced needle position;

wherein the needle stop prevents withdrawal of the distal portion of the needle into the catheter body upon flexure of the catheter prior to actuation of the advancement mechanism to advance the needle to the advanced needle position, thereby exposing a fixed length of the sharp tip of the needle;

(b) contacting the surface of the body cavity with the distal portion of the catheter, (c) advancing the sharp distal portion of the injector needle the controlled distance into the surface of the body cavity; and (d) introducing a therapeutic amount of a therapeutic fluid into the surface of the body cavity through the sharp tip of the injector needle.

In another embodiment, the present invention provides methods for promoting angiogenesis of an area of a heart by introducing an invention catheter into the interior of the heart through the vascular system of the subject; contacting the myocardium of the heart with the distal portion of the catheter; advancing the sharp distal portion of the injector needle the controlled distance into the myocardium; and introducing a therapeutic amount of an angiogenesis-promoting fluid a precisely controlled depth into the myocardium at multiple spaced locations through the sharp tip of the injector needle.

In another embodiment, the present invention provides methods for promoting angiogenesis of an area of a heart by introducing a hollow needle a precisely controlled distance into the epicardium of the heart of the subject during a surgical procedure, and injecting an angiogenesis promoting fluid comprising autologous bone marrow aspirate of the subject in a substantially sterile condition into the epicardium via the hollow needle at a plurality of spaced locations; wherein therapeutic fluid is introduced at a controlled depth in the range from about 0.1 cm to about 2 cm and wherein the volume of the fluid introduced at each of the locations is controlled to be in the range from about 0.1 ml to about 3.0 ml.

DETAILED DESCRIPTION OF THE INVENTION

Figure 1:
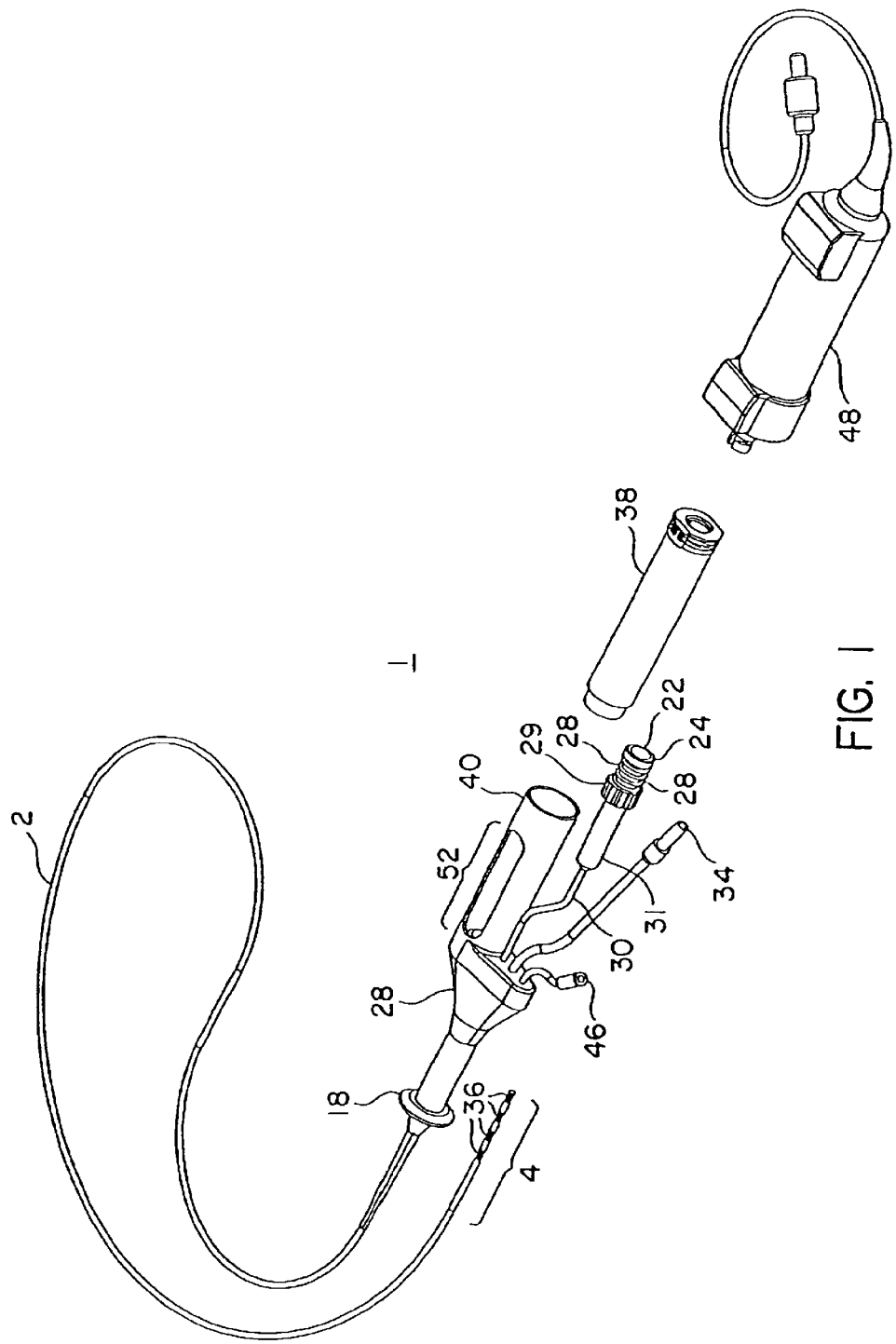
FIG. 1 is an exploded view drawing showing an exterior view of an assemblage comprising an invention deflection tip catheter with a handle-mounted sterile container as fluid source and motor-driven drug delivery actuator. The catheter has a handle-mounted canister for receiving the sterile container and a handle mounted needle actuator with depth stop and spring-loaded return.

The present invention relates generally to apparatus and methods for administering a therapeutic or diagnostic agent to an interior body cavity, especially the myocardium of the heart. Although the invention is described as particularly useful for administering a therapeutic or diagnostic agent to the myocardium, the methods and apparatus of the present invention may be used for administering therapeutic or diagnostic agents to the interior of other organs or vessels.

The invention catheter will now be described with reference to FIGS. 1–6 herein wherein reference numerals indicate the same device element in each of the Figures. The invention injection catheter 1 with controlled depth penetration comprises an elongate hollow catheter body 2 having a proximal end and a distal end with a distal flexible portion 4. The flexible distal portion 4 of the catheter body may have a shape memory or bias so the flexible tip assumes a predetermined shape when not within the confines of a narrow channel, such as a blood vessel. Alternatively, as shown in FIG. 3, a deflection mechanism 16 running within the catheter body can be attached distally to the flexible portion of the catheter body and to a tip deflection actuator 18 associated with the proximal end of the catheter body for causing the flexible portion to deflect curvilinearly.

It is also contemplated to be within the scope of the present invention that the invention catheter does not attach to the canister. In this embodiment, any fluid source can be attached via a fluid connector to the proximal end of the hollow needle.

Figure 5:
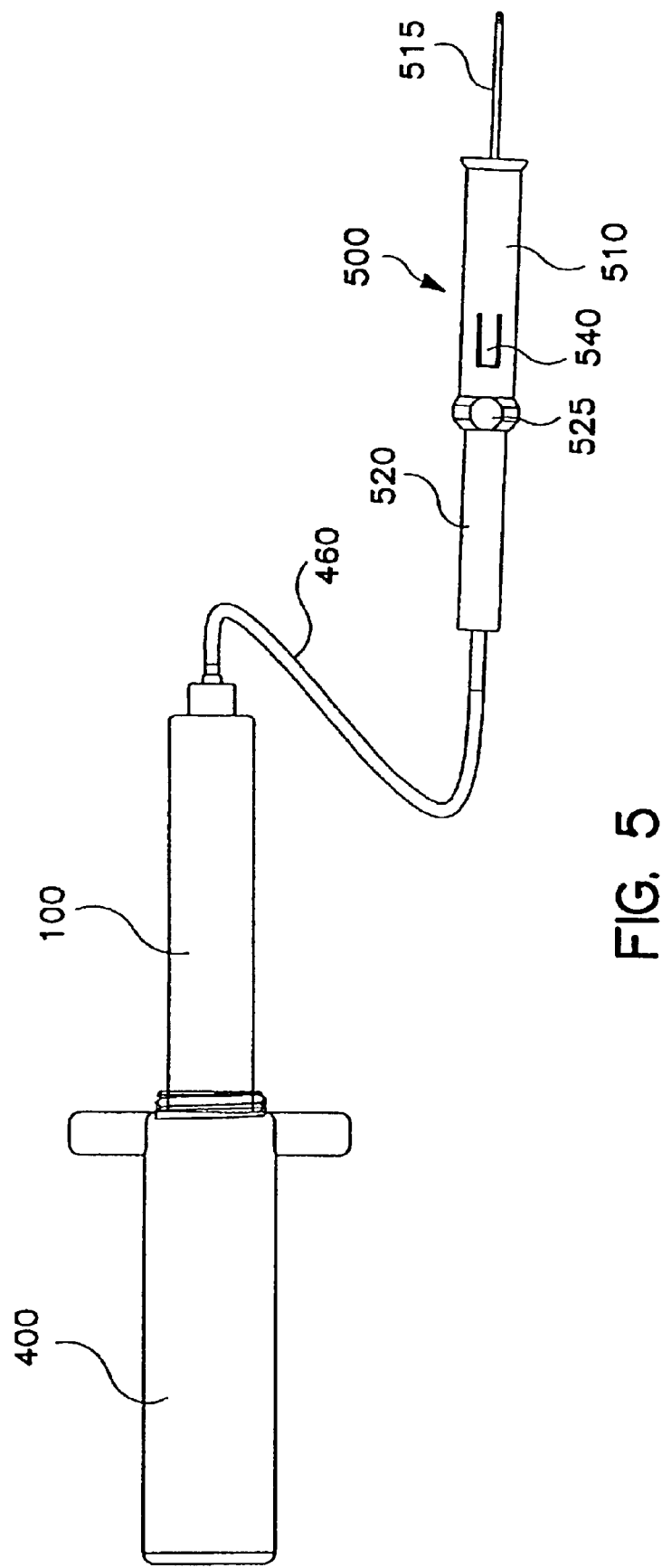
FIG. 5 is a schematic drawing showing an invention catheter with proximally fixed operator controlled adjustable needle stop that produces a sensible signal. The fluid source shown is a hand operated fluid delivery device with sensible signal that contains an invention sterile container.

As shown in FIG. 5, it is also contemplated to be within the scope of the present invention that the invention catheter does not have the handle-mounted canister. In this embodiment, any fluid source can be attached via a fluid connector to the proximal end of hollow needle 6. For example, the invention catheter can be attached to a hand-held sterile aspiration/reinjection system as described in detail in co copending U.S application Ser. No. 09/999,765, filed on even date herewith.

In addition, it may be convenient to connect the injection needle to the fluid source via flexible tubing, such as a plastic or polymer tubing, so that the fluid source can be remotely located with respect to the proximal end of the catheter. In this embodiment, the fluid source may be located in an invention sterile container held within a tabletop device, which may also contain a pressure actuator for ejecting sterile fluids from the sterile container into the proximal end of the invention catheter via the connecting flexible tubing. To effect a fluid-tight connection with the sterile container, in this assemblage the proximal end of the connecting tubing is provided with a fluid connector comprising a hollow needle cannula of sufficient length to puncture the sterile barrier located at the distal opening of the sterile container.

Figure 3:
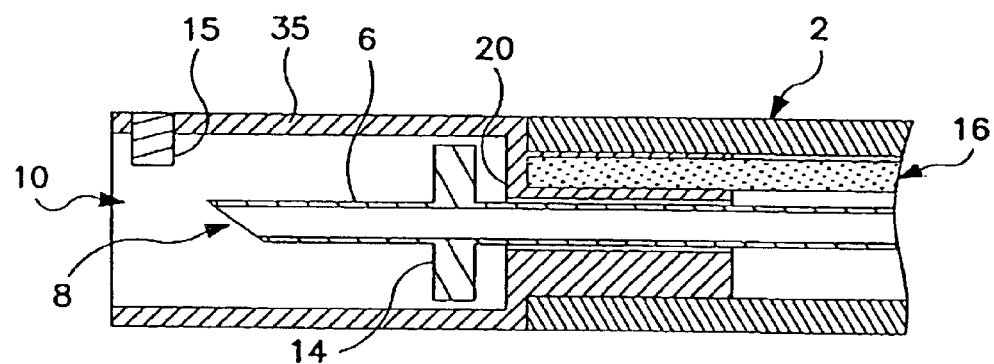
FIG. 3 shows a longitudinal section through the central axis of the distal portion of an invention catheter showing the sharp needle tip in the retracted position and the needle stop for prevention of needle withdrawal upon flexure of the catheter. The tip electrode housing is also shown.
Figure 4:
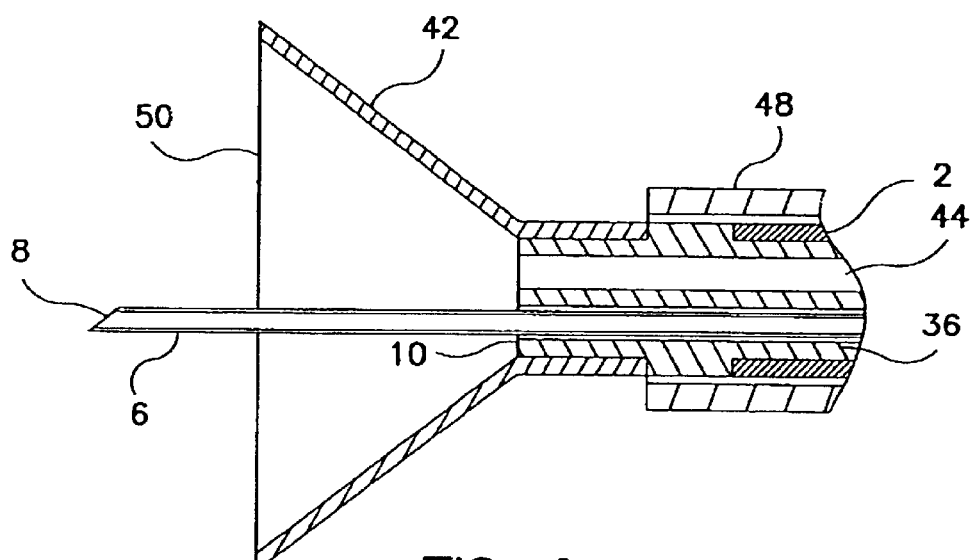
FIG. 4 shows a longitudinal section through the central axis of the distal portion of an invention catheter showing a suction lumen opening into a peripherally mounted suction cushion. A sheath that covers the suction cushion to retain the suction cushion in a folded condition has been withdrawn so that the suction cushion is unfolded and the distal tip of injection needle is shown in the advanced needle position.

As shown in FIG. 3, the hollow needle 6 has a retracted needle position with respect to the catheter body 2, wherein the sharp distal tip 8 of the needle is disposed within the catheter body, and an advanced needle position, shown in FIG. 4, wherein the sharp distal tip 8 of the needle extends a fixed distance beyond a distal end face 10 of the catheter body. As also shown in FIG. 3, needle 6 is provided with needle stop mechanism 14 to prevent withdrawal of the needle into the needle housing during flexure associated with positioning of the catheter for injection. Needle stop mechanism 14 may comprise one or more raised portions on the exterior of the needle and a retaining shoulder 20 in the interior of the catheter body against which the raised portions rest to prevent withdrawal of the distal portion of the needle when the tip deflection actuator is activated. Alternatively, a continuous lip on the exterior of the needle may abut against a shoulder within the interior of the catheter, e.g. attached to the interior surface of the catheter body to serve as the needle stop mechanism.

As described herein, the needle stop mechanism in the invention injection catheter tethers the distal end of the needle while the opposite, untethered end of the needle slides distally within the catheter body to provide any increase in needle length required to compensate for deflection of the needle. Deflection of the catheter will cause an increase in effective length in the range from about 0.2 cm to about 2.0 cm in a catheter of 30 cm in length. Therefore, it is preferred that the hollow needle in the invention catheter is longer than the catheter body by an amount at least as great the amount that the needle will slide proximally upon deflection of the catheter, for example about 0.2 cm to about 2.0 cm. This compensatory length 30 at the proximal end of the needle provides the advantage that the needle will not become disconnected from the fluid source attached at the proximal end thereof when the catheter flexes during insertion through the pathways of the vasculature. This is a departure from prior art deflectable injection catheters wherein the injection needle is fixed at the proximal end by attachment to a handle, fluid source or catheter housing, causing the sharp distal tip at the distal end to withdraw upon actuation of the tip deflection actuator.

The invention catheter further comprises an advancement mechanism attached to the needle and activated from the proximal end of the catheter for advancing the needle distally to the advanced needle position. The advancement mechanism is attached to the proximal end of hollow needle 6 and controls the distance of travel of the needle tip from the retracted needle position to the advanced needle position by advancing the slideably mounted needle distally a fixed distance. In FIG. 1, the advancement mechanism is shown as needle actuator 22, functions similarly to syringe. As shown in detail in FIG. 2, needle actuator 22 comprises depressible plunger 24, plunger housing 31, plunger depth stop 29, and spring 28. Upon depression, plunger 24 slides within plunger housing 31 until stopped by compression of spring 28 against depth stop 29. Spring 28 also provides a spring-loaded return feature when pressure on the plunger is released. Thus, the distance of travel of the needle within the catheter body is controlled by (e.g., proportional to or directly measured by) the distance of travel of the plunger as it is depressed from the extended position until travel is stopped by the plunger depth stop.

Preferably the position of the depth stop 29 on plunger housing 31 is adjustable. For example, the depth stop can be rotatably mounted on threads on the exterior of the plunger housing so that rotation of the depth stop alters the location of the depth stop and consequently the travel of the plunger into plunger housing 31. Thus, although the travel of the needle is a fixed distance at any one position of the adjustable plunger depth stop, the fixed distance is adjustable between different positions or settings of the depth stop. In another embodiment, the plunger may have mounted thereon a spring and a plunger coupling for securing the plunger in the plunger housing 31 when the spring is depressed. In this embodiment, the plunger includes an aperture in its base for connecting to a protrusion on the plunger. The plunger coupling is pushed against the spring by depression of the plunger, until it reaches a position wherein the plunger is spring-loaded and ready for release. Once the plunger is released, the spring urges the plunger backwards in a rapid motion, retracting the needle to the retracted needle position.

Figure 2:
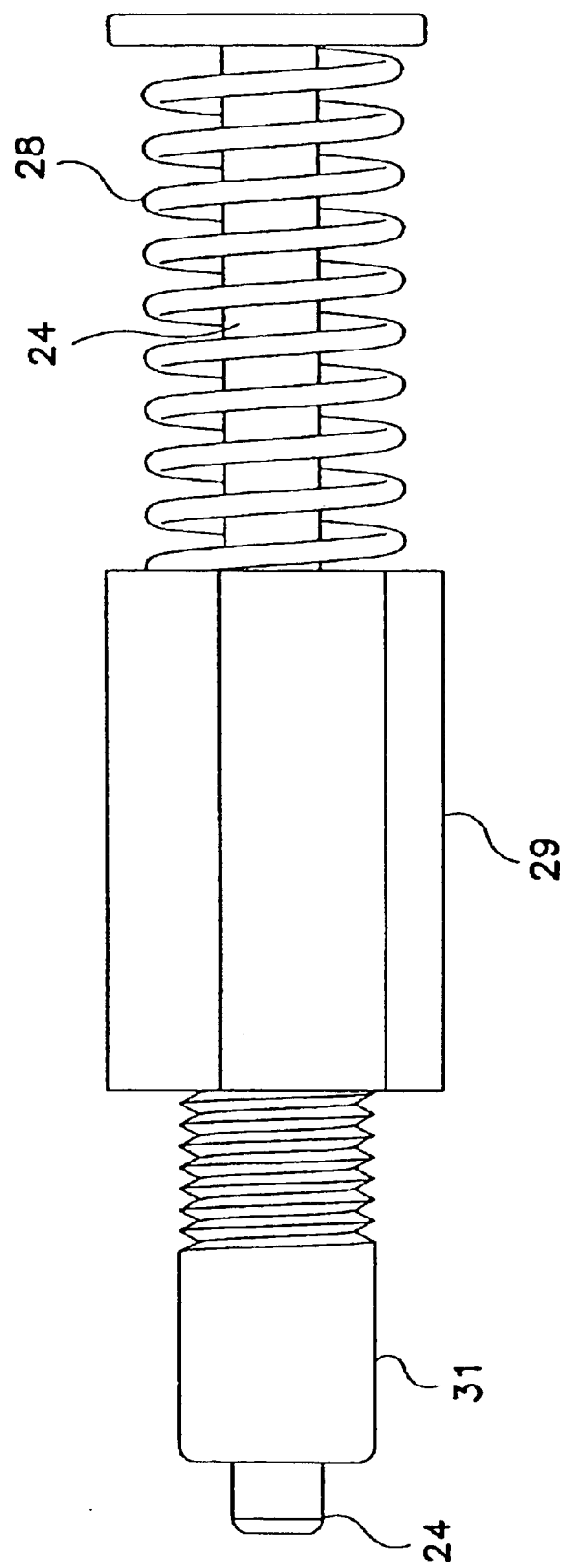
FIG. 2 is a drawing showing a detail of the needle actuator of FIG. 1 with adjustable depth stop and spring-loaded return.

Preferably the needle actuator 22 (e. g., the plunger/depth stop assembly as shown in FIGS. 1 and 2) is attached to the proximal end of distance compensator portion 30 at the proximal end of the freely slideable catheter needle 6. Thus, the needle actuator moves freely with movement of the proximal end of the needle to accommodate any variance in effective catheter length encountered during positioning due flexure (i.e. bending and/or deflection) of the catheter. An additional safety stop 15 can be positioned at the distal tip of the catheter body to limit the amount of distal movement "x" of the hollow needle when the needle actuator is actuated. In any case, advancement of the needle extends the needle tip not more than about 0.1 cm to about 2 cm beyond the end face 10 of the distal tip of the catheter body.

In use, flexure of the catheter may be accompanied by withdrawal of all or a part of the distance compensator portion 30 at the proximal end of needle 6 into the catheter body 2 as described herein, but the distal tip of the needle 6 is constrained by action of the needle stop 14. Flexure and sliding of the proximal end of the needle is allowed to take place prior to actuating the needle actuator. Once the catheter is satisfactorily positioned by the operator so that additional flexure is not contemplated, actuation of the needle actuator advances the needle tip 8 forward from the needle stop 14 a fixed distance to move the needle to the advanced needle position. After injection, the spring-loaded plunger/depth stop assembly is released by the operator to cause the needle to move to the retracted position for additional positioning of the distal tip of the catheter, for example at an additional injection site.

The invention catheters are sized and constructed to be advanced intravascularly into an interior body cavity of a subject. The catheter body can be constructed of any material typically used for such purpose, such as a flexible polymer or plastic. The proximal portion of the hollow injection needle is also manufactured of a material that is flexible while the sharp distal tip is manufactured of a hard metal, such as stainless steel, nitinol, and the like. The injection catheter is generally sized for threading through the patient's vasculature. For example, for insertion into the heart, the catheter is sized for percutaneous introduction by means of conventional cut-down techniques through the patient's arterial system, generally through the femoral artery. For ease in threading the distal tip of the invention catheter through the vasculature, the sharp distal tip of the needle in the retracted needle position is recessed within the catheter body (as shown in FIGS. 3) until the needle is advanced to the advanced needle position by actuation of the needle actuator mechanism.

In another embodiment, designed to aid in positioning the invention catheter at a remote location within a body cavity, as is shown in detail in FIG. 3, the distal tip of the catheter body can have an electroconductive tip portion 35 comprising one or more sensor electrodes 36, which can be used to determine contact between the needle tip and the tissue before the needle actuator is depressed to cause the needle to move the advanced needle position. The sensor electrodes 36 are electrically connected to an electrocardiogram or impedance meter. Since there are differences in the electrical impedance caused by air, blood, and heart tissue, a change in impedance as measured by an impedance meter attached to the sensor electrodes can be used to assure that the distal tip of the catheter is in contact with an interior surface, such as myocardium, before the needle is extended to the injection position. Alternatively, as is known in the art, if the electroconductive tip portion comprises multiple sensor electrodes 36 with multiple leads connected to an electrocardiogram (ECG), the electroconductive tip portion can be used to determine the depth of the needle penetration into tissue. In this configuration, the electrocardiogram is recorded from all leads. The larger signal is present from those ECG leads that are intramyocardial. In this embodiment of the invention catheter, one or more electrical leads can be threaded down a lumen of the catheter for attachment to an electrocardiogram or impedance meter via electrical connector 34 mounted at the proximal end of the catheter.

To further aid in the goal of injecting the therapeutic agent a controlled depth into a subject, it is desirable for the injection needle to penetrate tissue from an orientation approximately orthogonal to the tissue surface. Needle penetration depth (as measured orthogonally) and the length of needle penetration are equal only when such an orthogonal orientation is achieved prior to insertion of the needle tip into the tissue. Consequently, the actual depth of penetration of the needle is most precisely controlled if the needle enters the tissue approximately orthogonally to the tissue surface. The flexible distal portion of the invention catheter is adapted to deflect curvilinearly to aid in approaching walls of an interior body cavity where the walls do not lie in the same plane as the axis of the artery or vein through which the catheter has been threaded to reach the interior body cavity. For example, once the tip of the catheter is threaded through the vasculature into the interior cavity of the heart, the tissue most desirable for injection, the myocardium, it is necessary to deflect the tip of the catheter to address the walls approximately orthogonally.

An invention catheter can be designed to penetrate tissue any desired length by selecting a fixed length of exposed sharp distal needle tip (i.e., exposed beyond the distal end face of the catheter by actuation of the advancement mechanism) that is suitable to the thickness of the wall of the bodily cavity to be treated. For example, the length of the exposed needle tip should be sufficient to penetrate about 40% to 60% of the wall thickness of the interior cavity into which the catheter is to be used for injection of fluid.

In a one embodiment, the catheter is sized to inject a treatment fluid into the exterior or the interior of the heart (i.e., into epicardium or myocardium). In this embodiment, the fixed length of the exposed distal tip of the needle is selected according to the size and condition of the heart to be treated. For example, the myocardial wall typically has a thickness of about 8 to about 14 mm in an adult human. To prevent puncture of the myocardium and assure that the therapeutic fluid is delivered approximately midway through the myocardium, the length of the sharp distal tip should penetrate only about 3 mm to about 6 mm. However, for injection into a scared portion of myocardium, which typically will have a thickness of only 5 mm to 7 mm, an invention catheter having an exposed length of sharp distal tip of about 2.5 mm to about 3.5 mm would be selected. On the other hand, a hypertrophic heart may have a wall thickness of 20 mm or greater, so that an invention catheter having an exposed needle tip of up to about 8 mm to 10 mm would be used. The needle gauge can be selected to be any convenient size for the intended purpose. For example, for the purpose of injecting cells into the myocardium or epicardium, a 27-gauge needle is conveniently used. A 27-gauge needle having a length of one meter when filled with fluid will contain only about one cubic centimeter of fluid.

The distal tip of the needle used in the invention catheter can be straight (as shown) or can assume a curve of up to about 90 degrees as measured from the axis of the proximal portion of the needle when advanced to the extended needle position to facilitate epicardial injection on the back side of the heart (i.e., the side of the heart closest to the patient's spine). In the latter case, the distal tip of the hollow needle can contain a bias or memory that allows the flexible needle to be relatively straight until the distal tip is extended from the distal tip of the catheter body, at which time the distal tip will be free assume its biased curve.

In one embodiment, illustrated in FIG. 4, the invention injection catheter comprises a flexible suction lumen 44 running the length of the catheter body 2, which is in fluid-tight connection at the proximal end via a suction port 46 for attachment to a vacuum source. Opening 46 at the distal end of suction lumen 44 can be used to aid in positioning the distal end of the invention catheter prior to advancement of the needle 6 the controlled distance. Application of suction to the tissue surface via the suction lumen and suction port serves the function of assisting the operator to orient the needle's sharp distal tip orthogonally to the tissue surface.

As shown in FIG. 4, the opening 46 at the distal end of the suction lumen 46 opens into a fan-foldable, compressible suction cushion 42 that is attached to the periphery of the distal tip of the catheter body 2 and from which suction cushion 42 extends distally. A retractable sheath 48 having a retracted position and an unretracted position is slideably attached to the distal end of the catheter body 2. When in its unretracted position, the sheath covers the fan-foldable suction cushion 42 to maintain it in a folded state. When the sheath 48 slides proximally to its retracted position, as shown in FIGS. 3 and 4, the suction cushion 42 is freed from restraint, allowing the suction cushion to unfold to assume an expanded, readily compressible shape. Typically a retraction element attached to the sheath 48 and to the proximal end of the catheter body (or to the handle 28), optionally spring-loaded, is used to slide the sheath proximally to uncover the suction cushion.

The expanded or unfolded suction cushion can assume any shape and size that will spread the partial vacuum applied via the suction port over a larger surface area than the face of suction opening 46 so as to avoid damage to the tissue surface (e.g., the myocardium) that might result if the suction port were to directly contact the tissue surface. For example, the cross-sectional area of the open end face 50 of the unfolded suction cushion can be 2 to 10-fold or more larger than the cross-sectional area of opening 46 of the suction lumen. In one embodiment, as shown in FIG. 4, the expanded suction cushion can be designed to assume the shape of an outwardly diverging compressible cone in its unfolded state.

Optionally, the hollow injection needle can be threaded through the suction lumen 44 in the catheter body 2, and the shoulder 20 against which the needle stop 14 on the needle abuts is located on the interior of the suction lumen. Consequently, in this embodiment, the hollow needle is advanced and retracted by sliding through the suction lumen. In one embodiment, in the advanced position of the needle, the sharp distal tip 8 does not extend beyond the end face of the suction cushion 42 (whether the sheath has been retracted or not) until the suction cushion is compressed, for example by pressing against a tissue surface.

The suction cushion is made of a flexible, readily compressible substance, such as a soft rubber, or elastomeric material that can be readily compressed to expose the sharp distal tip of the hollow needle. In use, a partial vacuum from a vacuum source is applied via the suction lumen 44 and suction port 46 to the open end face 50 of the suction cushion 42. As the suction cushion is drawn into contact with a tissue surface by application of suction and manipulation of the catheter by the operator, the suction cushion will compress sufficiently to allow the fixed length of sharp distal tip of the injection needle to penetrate the tissue surface. At the same time, a portion of tissue surface contacted by the suction cushion may be drawn into (e.g. intrude) the open end face 50 of the suction cushion 42 to facilitate penetration of the needle the full fixed length of the extended sharp distal tip.

As shown in FIG. 1, handle 28 of the invention catheter includes a distal portion joined to catheter body 2, and a proximal portion to which the needle actuator 22 and suction port 46 are attached. Also attached to the proximal portion of the handle 28 is a fluid source connector for attachment of the proximal end of the hollow needle to a fluid source. In embodiments wherein the invention catheter has one or more sensor electrodes 36 at the distal tip, an electrical connector 34 is attached to the proximal portion of the handle 28 for connection of the electrical lead to an electrocardiogram or impedance meter. In the embodiments shown in FIG. 1, the fluid source connector comprises a handle-mounted cylindrical canister 40 shaped to receive an invention sterile container 38. The wall of the canister may be provided with a sight window 52 to allow easy visual confirmation of the presence of the sterile container and/or the contents of the sterile container, especially if the sterile container is made of a transparent or semi-transparent material. The sterile container 38 is provided with a sterile barrier at the distal end thereof. In this assemblage, positioned between the proximal end of the catheter injection needle 6 and the distal end of the sterile container 38 is a fluid connector that includes a needle cannula for piercing the sterile barrier at the opening of the sterile container and a locking mechanism, such as a luer lock, for removably attaching the distal end of the sterile container in fluid-tight connection to the catheter injection needle 6. In this configuration, fluids expressed from the sterile container can be injected via the hollow needle in the catheter. The assemblage may further comprise an invention motor-driven actuator (i.e. a drug delivery actuator 48) for expressing fluids in controlled amounts from the sterile container. Preferably, the drug delivery actuator drives a plunger housed within the sterile container to express fluids into the catheter injection needle. Alternatively, as described herein, a fluid source, such as a syringe containing a therapeutic fluid, can be coupled to the fluid connector on the proximal portion of the catheter handle, for example, via a hub on the syringe.

As also shown in FIG. 1, a tip deflection actuator 18 can be attached to the proximal end of catheter body, that is operable to deflect the flexible distal portion 4 of the invention catheter. Actuation of the tip deflection actuator 18 in the invention device causes the flexible distal portion to coil curvilinearly. In addition, when in the coiled conformation, the coiled flexible tip of the catheter body and the remainder of the catheter body generally lie substantially in a single plane. However, in an alternative embodiment, the deflection mechanism attached to the flexible portion of the catheter body and to the tip deflection actuator associated with the proximal end of the catheter body are configured to cause the flexible tip of the catheter body to rotate into a plane that lies at an angle to the remainder of the catheter body as the tip deflection actuator is actuated.

The tip deflection mechanism 16 running between the flexible tip 4 of the catheter body and the tip deflection actuator 18 can be of any type known in the art, such as a cable system running down the interior of the catheter body wherein the tip deflection actuator, which may be a rotatable handle (as shown), a crank or like means, is used to adjust the cable system so as to cause the flexible tip to move deflect, e.g., curvilinearly.

Generally, the flexible portion of the catheter body comprises an articulation section, such as a tubular covering having a pattern of circumferential slits therein which act as vertebrae for articulation of the flexible distal portion. The vertebrae may or may not be hinged together, and are threaded over one or more pull wires. When tension in a pull wire is increased by manipulation of the proximal tip deflection actuator, the vertebrae are forced together on the side associated with the particular wire, causing the assembly to bend in that direction. As many as four-ways of articulation can be achieved in such deflectable endoscopic devices as described in U.S. Pat. No. 5,846,173, which is incorporated herein by reference in its entirety.

For example, in one embodiment the flexible distal portion of the deflectable injection catheter can be selectively curved by controllably moving one of three flat sandwiched shims relative to the others by manipulation of a handle portion as tip deflection actuator, as described more fully in U.S. Pat. No. 5,190,050, which is incorporated herein by reference in its entirety. In other embodiments, such as described more fully in U.S. Pat. No. 5,358,479, which is incorporated herein by reference in its entirety, the flexible tip of the invention device can be coiled by means of a single elongated, substantially flat shim spring mounted within the flexible tip as the deflection mechanism. The shim has at least one transverse or lateral twist that causes the tip of the rod to assume a desired curvature upon operation of the tip deflection actuator.

Figure 6:
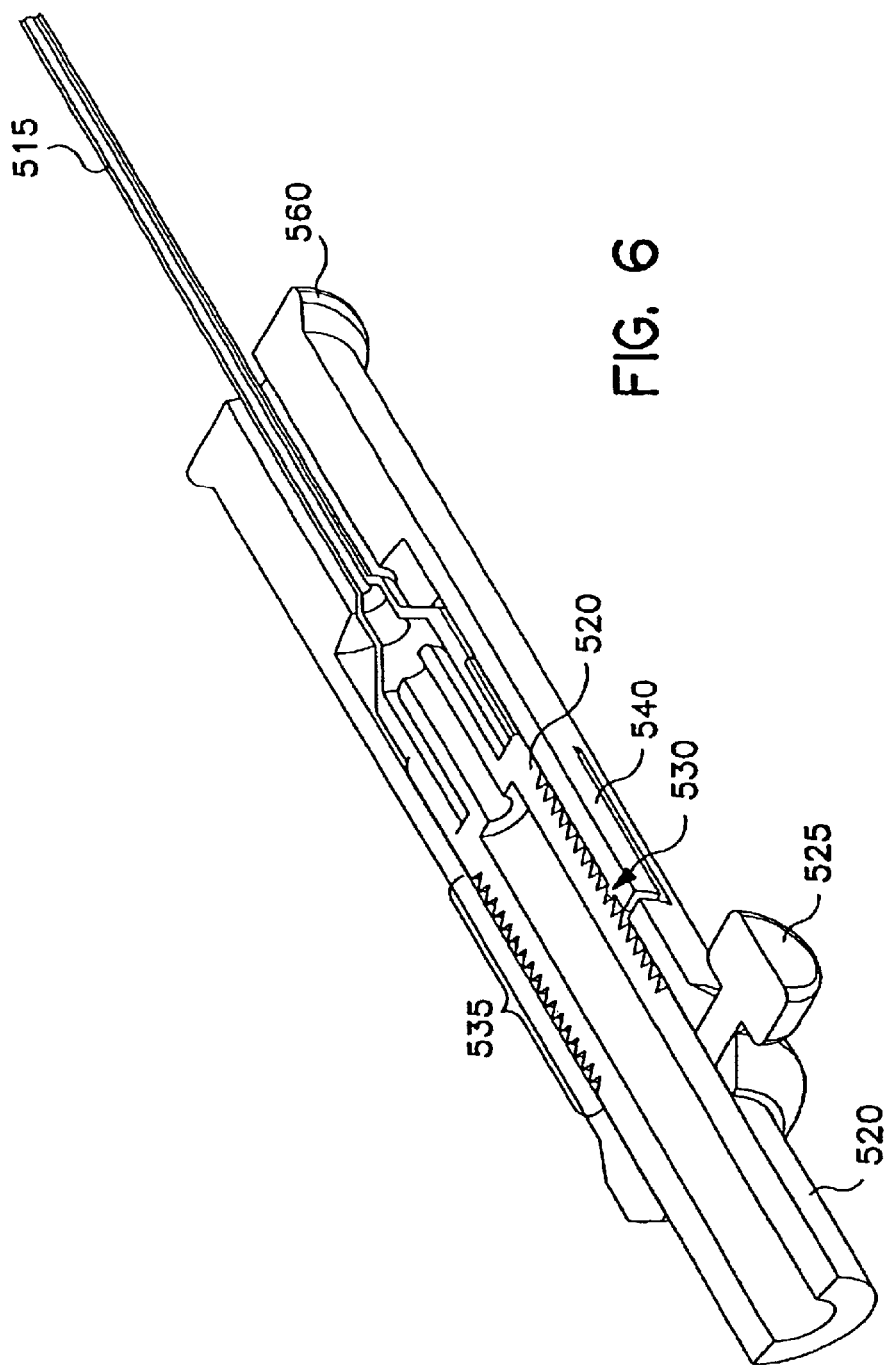
FIG. 6 is a schematic drawing showing a longitudinal cross-section of the invention operator controlled adjustable needle stop shown in FIG. 5.

In a preferred embodiment, shown in FIG. 6, the adjustable needle stop 500 encloses the proximal portion of injection needle 515 and comprises in co-axial arrangement a substantially cylindrical outer needle holder 510, and a needle carriage 520 having an interior shaped to receive the proximal portion of the injection needle 515 (shown in cut-away) to which the needle carriage is fixedly attached. Preferably, the distal end of the needle holder 510 is bell-shaped with a substantially flat distal end face 560 from which the distal tip of the needle protrudes when the needle is advanced from the recessed position into one of a series of possible advanced positions. The flat distal end face 560 helps to orient the needle orthogonally to the tissue surface for injection.

In a preferred embodiment, shown in FIG. 6, the adjustable needle stop 500 encloses the distal portion of injection needle 515 and comprises in co-axial arrangement a substantially cylindrical outer needle holder 510, and a needle carriage 520 having an interior shaped to receive the distal portion 515 of the injection needle (shown in cut-away) to which the needle carriage is fixedly attached. Preferably, the distal end of the needle holder is bell-shaped with a substantially flat distal end face 560 from which the distal tip of the needle protrudes when the needle is advanced from the recessed position into one of a series of possible the advanced positions. The flat distal end face 560 helps to orient the needle orthogonally to the tissue surface for injection.

The needle carriage 520 is slideably mounted within the needle holder 510 for movement between a fully recessed position, in which the distal tip of the needle does not protrude from the distal end of the needle holder, and a series of progressively advanced positions, in which the distal tip of the needle is progressively advanced to expose the precisely controlled increments of the distal tip thereof. A locking mechanism 525, shown as a tightening screw, is provided for locking the position of the needle carriage with respect to the needle holder during use of the needle for injections.

As shown in longitudinal cross-section in FIG. 5, the mechanism for providing a sensible signal in the invention adjustable needle holder can comprise an internally protruding flexible detent 540 mounted at the proximal end of the outer needle holder 510 and threads 535 (forming a series of precisely spaced series of circumferential notches) along the exterior length of the needle carriage 520. The needle tip can be advanced proximally in two different ways. The needle carriage 520 to which the needle is fixedly attached can be advanced proximally by rotation of the needle holder 510 about needle carriage 520 while detent 540 rides along threads 535. As indicator of the length of needle tip exposed, calibrated markings can be provided on the exterior of the needle carriage, for example at 0.5 millimeter intervals, by which the operator can visually judge the amount of needle tip that has been exposed by rotation of the needle holder.

Alternatively, needle carriage 520 can be advanced proximally by sliding the needle carriage within holder 510 such that threads 535 (i.e., a series of precisely spaced circumferential "notches") sequentially receive nub 530 on flexible detent 540, causing the detent to move from one thread valley (or "notch") to the next thread valley (or "notch") along the series of threads 535. Sliding the needle proximally as above described emits an audible and/or tactile signal as indicator each time the detent moves from thread valley to thread valley. Thus, in operation the mechanism for generating the audible and/or tactile signal functions in a manner similar to a thumb nail being drawn across the tips of the teeth of a comb.

Preferably, an arcuate cut out flap 540 in the side of the needle holder at the proximal end thereof has an internal protrusion 530 at the apex of the arcuate flap that forms detent 540. In this embodiment, the needle holder is preferably molded or cast from a material, such as a plastic or polymer, having sufficient flexibility that the U-shaped flap with attached detent forms a continuous piece with the body of the needle holder. If the needle carriage is cast or molded, a precision grinder can be used to create the precisely spaced series of notches 535 on the exterior of the needle carriage.

For example, the location of the first thread valley in the series of thread valleys can correspond to the needle being in the fully recessed position and the distance between threads 535 can be precisely controlled such that each 360° rotation or each audible and/or tactile signal (or "click") caused by advancement of the needle carriage corresponds to one desired increment of needle tip protrusion. For example, if the threads (or "notches") are precisely spaced at 0.5 mm intervals, movement of the needle carriage forward from the fully recessed position sufficient to create 3 signals indicates that the needle tip has been exposed exactly 1.5 mm. Thus, the adjustable needle stop 500 can be designed such that the operator precisely and easily controls the depth to which the needle tip of the invention catheter penetrates a tissue surface for an injection and the operator can readily adjust the depth of needle penetration during a surgical procedure between injection sites by sliding or rotating the needle holder to expose or retract the needle tip, for example by counting a desired number of "clicks."

The present invention further provides methods for injecting a therapeutic fluid a controlled distance into the surface of an interior body cavity in a subject in need thereof. In one embodiment, the invention method comprises introducing an invention injection catheter into the interior body cavity by advancing the catheter through the vascular system of the subject into the interior body cavity; positioning the distal end of the catheter within the body cavity so as to contact the surface of the body cavity; and advancing the exposed sharp distal tip of the injector needle the fixed distance into the surface of the body cavity wherein the fixed distance is from 40% to 60% of the thickness of the wall of the body cavity. A therapeutic amount of a therapeutic fluid can then be introduced into the surface of the body cavity through the sharp distal tip of the injector needle.

Preferably, the sharp distal tip is advanced orthogonally into the surface of the body cavity and a controlled amount of the fluid is administered the fixed distance into the surface of the bodily cavity by the invention methods. For example the amount of fluid injected according to the invention method can be controlled automatically by a control system attached to the proximal end of the catheter body, such as the motor-driven drug delivery actuator shown in FIG. 1. The control system may further comprise a computer system with a processor and one or more internal data storage components for storing data, and one or more data retrieving devices for retrieving the data stored on the data storage components. The computer is operable to control the amount of the therapeutic liquid (e.g., angiogenic agent) introduced into the catheter from the fluid source, for example by controlling advancement of a stepper motor-driven piston within an invention actuator or other type of syringe-type fluid source so as to expel a predetermined amount of fluid from the fluid source. A skilled artisan can readily appreciate that any one of the currently available computer systems are suitable.

The interior body cavity in the invention method is preferably a heart, and the catheter is advanced percutaneously into the heart and positioned so as to contact the myocardium or the invention catheter is used to provide controlled depth penetration injections into the epicardium, for example, during a cardiac surgery. For percutaneous delivery, as described above more fully, control of the exact amount of fluid injected is facilitated by deflecting the invention catheter such that the exposed sharp distal tip contacts the surface of the body cavity approximately orthogonally. For this purpose, an invention catheter having a suction lumen in the catheter body with a compressible suction cushion attached to the distal end of the catheter body may be utilized. In this case, suction (i.e., a negative pressure) is applied via the suction lumen and suction port to the suction cushion at the distal end of the catheter as the operator manipulates the distal portion of the catheter into place. The suction is used to help orient the distal portion of the catheter approximately orthogonally to the surface of the bodily cavity to be injected. The amount of suction to be applied to the tissue surface will be an amount per unit of surface area, as determined by those of skill in the art, that will not scar or cause irreversible damage to the tissue surface. The suction cushion, which is sized to apply the suction to the tissue surface over a larger area than the cross-sectional area of the suction lumen, is effective for reducing the risk of damage to the tissue surface. The amount of suction applied to the myocardial surface according to the present invention methods is in the range from about 50 mmHg per square centimeter to about 500 mmHg per square centimeter.

Alternatively, the invention catheter having sensor electrodes at the distal tip in electrical connection with an electrocardiogram of impedance meter may be introduced into the heart. When such a catheter is used, the sensor electrodes are used to determine when the deflectable tip of the catheter touches the myocardium by reading a change in EKG signal or in impedance on the impedance meter. Once contact with the myocardium is confirmed by such methods, the needle in the invention catheter may be advanced a controlled distance to the advanced needle position by actuation of the needle actuator with plunger depth stop.

Alternatively, the invention provides methods for introducing therapeutic fluids (e.g, containing autologous bone marrow aspirate) with controlled depth penetration without percutaneous delivery, for example into a body cavity exposed during a surgical procedure. In this embodiment, the invention methods can utilize a tissue injection catheter having a hollow needle to which is attached an operator controlled adjustable needle stop with sensible signal, as described herein (See FIGS. 5 and 6).

In any of the invention methods, the therapeutic fluids to be delivered can be contained in a sterile container (for example sterile container 38 housed in the handle-mounted canister 40 shown in FIG. 1), which is in fluid communication with the proximal end of the injection needle. As shown in FIG. 1, the canister holds the sterile container stationary to facilitate fluid connection between the fluid contents of the sterile container and the hollow needle during percutaneous injections. As shown in FIGS. 1 and 6, a pressure actuator (or drug delivery actuator) attached to the proximal end of the sterile container expels treatment fluid from the sterile container into the catheter in precisely controlled volumes. The pressure actuator can be motor-driven or hand-operated.

When this assemblage is used in practice of the invention methods, once the needle is advanced into target tissue the controlled distance, the pressure actuator is activated. For example, in the embodiment shown in FIG. 1, delivery actuator 48 is activated so as to advance the piston therein a distance sufficient to express a predetermined amount of treatment fluids from the sterile container into the injection needle and from thence into myocardial tissue. Similarly, in the embodiment shown in FIG. 5, a hand-operated delivery actuator is used to express one or more predetermined volumes of treatment fluid from the sterile container into the hollow needle of the injection catheter. The embodiment shown in FIG. 5 is preferred for epicardial injection during open heart surgery and for similar situations wherein the treatment site is surgically exposed.

For injection of an angiogenic fluid into the myocardium or epicardium of the heart according to the invention methods, the fixed distance to which the exposed needle distal tip is advanced into the tissue surface is about 40–50% of the wall thickness or about 2.5 mm to about 10 mm, depending upon the thickness of the tissue at the injection site, which can range from about 5 mm for a scared zone to about 20 mm in a hypertrophic heart. The amount of angiogenic fluid injected at any site is about 0.1 ml to 3.0 ml per injection site, for example 0.5 ml to about 2.0 ml. Generally the angiogenic fluid is injected at a plurality of spaced locations on the surface of the myocardium or epicardium, for example about 10 to 24 different injection sites for the purpose of promoting transmyocardial revascularization.

The therapeutic fluid injected according to the invention method will be selected by the skilled practitioner to promote any desired therapeutic goal that is facilitated by injection to a predetermined depth of a controlled amount of a therapeutic fluid, such as one comprising a polypeptide, a peptide, a chemotherapeutic agent, or a polynucleotide that encodes a therapeutic agent, and the like. The polynucleotide can be selected from DNA, cDNA and RNA and can optionally be injected in any convenient form, such as incorporated into plasmid DNA, in a viral vector, incorporated into a liposome, and the like.

In a preferred embodiment of the invention methods, the therapeutic fluid used for transmyocardial revascularization is an angiogenic fluid, for example a fluid preparation containing one or more transcription factors, angiogenesis factors, myogenesis factors or growth factors suitable for promoting angiogenesis, and the like. Among the presently preferred angiogenesis promoting agents are human vascular endothelial growth factor (VEGF) and/or basic fibroblast growth factor (bFGF) or a polynucleotide encoding VEGF, bFGF, platelet-derived endothelial growth factor (PD-ECGF), endothelial growth factor (EGF), tissue necrosis factor alpha (TNFα), tissue growth factor alpha (TGFα). Alternatively, one or a mixture of polynucleotides encoding such agents can be introduced as naked DNA or in a delivery vehicle, such as a replication-deficient adenovirus. Additional angiogenesis promoting agents presently preferred for injection according to the invention methods include bone marrow aspirate, bone marrow cells, and angioblasts.

The invention method may be incorporated into any type of cardiac surgical procedure. For example the invention catheter may be introduced into the interior of the heart during beating heart surgery. To aid in introduction of the catheter into the heart, a sheath with a dilator inside may first be introduced into a chamber of the heart and the dilator activated to increase access into the interior chamber of the heart. Then the dilator can be removed and the invention catheter introduced into the chamber of the heart via the sheath. Alternatively, revascularization fluids can be delivered epicardially during any type of cardiac surgery wherein the chest is opened, such as during surgery to create an anastomosis, i.e., by-pass surgery.

The subject of the invention method may be any mammalian species, such as a domestic pet or animal raised or bred for economic gain, but the subject is preferably a human.

The present invention may be embodied in other specific forms without departing from the spirit or central attributes thereof. Thus, the foregoing description of the present invention discloses only exemplary embodiments thereof, and other variations are contemplated as being within the scope of the present invention. Accordingly, the present invention is not limited to the particular embodiments that have been described in detail herein. Rather, reference should be made to the appended claims as indicative of the scope and content of the invention.

What is claimed is:

1. A method for injecting a therapeutic fluid a controlled distance into the surface of an interior body cavity in a subject in need thereof, said method comprising:

(a) introducing a catheter into the interior of a body cavity by advancing the catheter through the vascular system of the subject, said catheter comprising:

i) an elongate hollow catheter body having a proximal end and a distal end with a flexible portion at the distal end thereof, said catheter body being sized and constructed to be advanced intravascularly into an interior body cavity of a subject;

ii) a hollow needle housed throughout the catheter body, said needle having a distal portion with a sharp tip and a proximal portion in fluid communication with a fluid source, said needle further having a retracted needle position wherein the sharp tip of the needle is disposed within the catheter body, and an advanced needle position wherein the sharp tip of the needle extends a fixed distance beyond a distal end face of the catheter body, iii) a needle stop attached to the needle that tethers the distal portion of the needle during flexure while the proximal portion of the needle remains freely slideable within the catheter body, and iv) an advancement mechanism attached to the needle for advancing the needle distally a fixed distance to the advanced needle position; wherein the needle stop prevents withdrawal of the distal portion of the needle into the catheter body upon flexure of the catheter prior to actuation of the advancement mechanism to advance the needle to the advanced needle position, thereby exposing a fixed length of the sharp tip of the needle;

(b) contacting the surface of the body cavity with the distal end face of the catheter body, (c) advancing the sharp distal portion of the hollow needle the controlled distance into the surface of the body cavity; and (d) introducing a therapeutic amount of a therapeutic fluid into the surface of the body cavity through the sharp tip of the hollow needle.

2. The method of claim 1, wherein a controlled amount of the fluid is administered.

3. The method of claim 1, wherein the controlled amount is in the range from about 0.1 ml to about 3 ml.

4. The method of claim 1, wherein the therapeutic fluid is introduced into the musculature of the heart.

5. The method of claim 4, wherein the catheter is attached to a source of substantially sterile fluid comprising cells autologous to the subject and the body cavity is the interior of the heart of the subject.

6. The method of claim 1, wherein the sharp distal portion of the needle is advanced into the surface a distance in the range from about 0.1 cm to about 2.0 cm.

7. The method of claim 5, wherein the surface is the myocardium of the heart of the subject.

8. The method of claim 7 wherein the method is repeated such that the fluid is administered at a plurality of spaced locations on the myocardium to promote transmyocardial revascularization.

9. The method of claim 8, wherein the amount of the fluid injected is controlled to be in the range from about 0.05 ml to about 5 ml at each of the spaced locations.

10. The method of claim 8, wherein the catheter is introduced into the interior of the heart during a cardiac surgical procedure.

11. The method of claim 10 wherein the catheter is introduced into the interior of the heart during beating heart surgery.

12. The method of claim 5, wherein the fluid further comprises one or more growth factors suitable for stimulating angiogenesis.

13. The method of claim 12, wherein the growth factor is selected from the group consisting of human vascular endothelial growth factor (VEGF), basic fibroblast growth factor (bFGF), and HIF-1.

14. The method of claim 5, wherein the fluid contains at least one polynucleotide encoding a growth factor suitable for stimulating angiogenesis.

15. The method of claim 14 wherein the polynucleotide encodes a growth factor selected from the group consisting of VEGF, bFGF, and HIF-1.

16. The method of claim 14 wherein the polynucleotide encodes a growth factor selected from the group consisting of PD-ECGF, EGF, TNFα, and TGFα.

17. The method of claim 1, wherein the fluid comprises autologous bone marrow aspirate or bone marrow cells in a substantially sterile condition.

18. The method of claim 1, wherein the fluid comprises autologous bone marrow cells in a substantially sterile condition.

19. The method of claim 18, wherein the bone marrow cells comprise angioblasts.

20. The method of claim 5, wherein the amount of the fluid introduced is precisely controlled by a pressure actuator in communication with the fluid source.

21. The method of claim 1, wherein the subject is a human.

22. The method of claim 1, wherein the catheter further comprises a deflection mechanism operable from the exterior of the catheter body via a tip deflector actuator for causing the distal flexible portion to deflect curvilinearly to address the surface.

23. The method of claim 1, wherein the advancement mechanism of the catheter comprises a needle actuator having a depressible plunger with plunger depth stop and spring-loaded return, wherein the plunger is depressed to advance the sharp distal portion of the injector needle controlled distance into the surface of the body cavity.

24. The method of claim 5, wherein the catheter further comprises an electroconductive tip portion at the distal tip of the catheter body that is electrically connected to an electrical connector at the proximal portion of the catheter body and wherein the method further comprises using the electroconductive tip to determine when the distal end of the catheter contacts the surface of the myocardium.

25. A method for promoting angiogenesis of an area of a heart, said method comprising:
(a) introducing a catheter into the interior of the heart by advancing the catheter through the vascular system of the subject, said catheter comprising:
    i) an elongate hollow catheter body having a proximal end and a distal end with a flexible portion at the distal end thereof, said catheter body being sized and constructed to be advanced intravascularly into an interior body cavity of a subject;
    ii) a hollow needle housed throughout the catheter body, said needle having a distal portion with a sharp tip and a proximal portion in fluid communication with a fluid source, said needle further having a retracted needle position wherein the sharp tip of the needle is disposed within the catheter body, and an advanced needle position wherein the sharp tip of the needle extends a fixed distance beyond a distal end face of the catheter body,
    iii) a needle stop attached to the needle that tethers the distal portion of needle during flexure while the proximal portion of the needle remains freely slideable within the catheter body, and
    iv) an advancement mechanism attached to the needle for advancing the needle distally a fixed distance to the advanced needle position;
wherein the needle stop prevents withdrawal of the distal portion of the needle into the catheter body upon flexure of the catheter prior to actuation of the advancement mechanism to advance the needle to the advanced needle position, thereby exposing a fixed length of the sharp tip of the needle;
(b) contacting the myocardium of the heart with the distal end face of the catheter body;
(c) advancing the sharp distal portion of the hollow needle the controlled distance into the myocardium; and
(d) introducing a therapeutic amount of an angiogenesis-promoting fluid a precisely controlled depth into the myocardium at multiple spaced locations through the sharp tip of the hollow needle.

26. The method of claim 25, wherein the angiogenesis promoting fluid comprises cells autologous to the subject and the fluid is in a substantially sterile condition.

27. The method of claim 26, wherein the amount of the angiogenesis-promoting fluid is precisely controlled to be in the range from about 0.1 ml to about 3 ml.

28. The method of claim 27, wherein the controlled distance is in the range from about 0.1 cm to about 2.0 cm.

29. The method of claim 28, wherein the method is repeated such that the angiogenesis-promoting fluid is administered at a plurality of spaced locations on the myocardium to promote transmyocardial revascularization.

30. A method for promoting angiogenesis of an area of a heart, said method comprising:
(a) introducing a hollow needle housed throughout a catheter body a precisely controlled distance into the epicardium of the heart of the subject during a surgical procedure, the needle having a needle stop that tethers the distal portion of the needle during flexure while the proximal portion of the needle remains freely slidable within the catheter body, and (b) injecting an angiogenesis promoting fluid comprising autologous bone marrow aspirate of the subject in a substantially sterile condition into the epicardium via the hollow needle at a plurality of spaced locations; wherein therapeutic fluid is introduced at a controlled depth in the range from about 0.1 cm to about 2 cm and wherein the volume of the fluid introduced at each of the locations is controlled to be in the range from about 0.1 ml to about 2.0 ml.

31. The method of claim 30 wherein the hollow needle is contained in an injection catheter and wherein the depth of needle penetration is controlled by an operator-controlled adjustable needle stop fixedly attached to distal portion of the needle, and wherein the method further comprises the operator exposing one or more precisely controlled increments of the distal tip of the needle by sliding the needle distally through one or more of a series of positions within the needle stop and wherein the needle stop provides a sensible signal to the operator that indicates how many of the precisely controlled increments of the distal tip have been extended from within the needle stop by the operator sliding the needle distally and wherein the depth of needle penetration is controlled by the length of the distal tip of the needle exposed by the operator.

32. The method of claim 30, wherein the adjustable needle stop comprises in co-axial arrangement:

a substantially cylindrical outer needle holder, and a needle carriage having an interior shaped to receive the distal portion of the injection needle, said needle carriage being slideably mounted within the needle holder for movement between a recessed position, in which the distal tip of the needle does not protrude from the distal end of the needle holder, and a series of progressively advanced positions, in which the distal tip of the needle is advanced to expose the precisely controlled increments of the distal tip thereof; and a locking mechanism for locking longitudinal movement of the needle carriage within the needle holder.

33. The method of claim 31, wherein each sensible signal corresponds to advancement of the needle tip an increment of 0.5 mm to about 2.0 mm.

34. The system of claim 31, wherein the sensible signal is a flash of light.

35. The system of claim 31, wherein the sensible signal is an audible and/or tactile signal.

36. The system of claim 32, wherein the needle holder comprises a flexible detent extending from the proximal end of the holder, and the exterior of the needle carriage comprises a longitudinal series of circumferential notches shaped to sequentially receive the flexible detent as the needle carriage slides within the needle holder, causing the detent to move from one notch to an adjoining notch along the series of circumferential notches so as to generate the audible and/or tactile signal.

37. The method of claim 32, wherein the amount of the angiogenesis-promoting fluid is precisely controlled to be in the range from about 0.1 ml to about 1 ml.

38. The method of claim 32, wherein the controlled distance is in the range from about 0.1 cm to about 2.0 cm.

* * * * *